United States Patent [19]

Ort et al.

[11] Patent Number: 5,441,922
[45] Date of Patent: Aug. 15, 1995

[54] COMBINATIONS OF BENZOYL CYCLOHEXANEDIONE HERBICIDES AND CROP-PROTECTING SUBSTANCES

[75] Inventors: Oswald Ort, Kelkheim; Lothar Willms, Hillscheid; Hans-Joachim Zeiss, Sulzbach/Tanus; Stephan Mller; Herbert Stark, both of Kelkheim; Rainer Schütze, Idstein/Taunus; Klaus Bauer, Hanau; Hermann Bieringer, Eppstein/Taunus, all of Germany

[73] Assignee: Hoechst Aktiengesellschaft, Frankfurt am Main, Germany

[21] Appl. No.: 998,009

[22] Filed: Dec. 29, 1992

[30] Foreign Application Priority Data

Dec. 31, 1991 [DE] Germany .................. 41 43 253.3

[51] Int. Cl.6 .................. A01N 25/32; A01N 43/42; A01N 43/80; A01N 43/56
[52] U.S. Cl. .................. 504/104; 504/105; 504/106; 504/108
[58] Field of Search .......... 504/105, 104, 106, 108

[56] References Cited

U.S. PATENT DOCUMENTS

| | | | |
|---|---|---|---|
| 3,950,420 | 4/1976 | Sawaki et al. | 504/337 |
| 4,639,266 | 1/1987 | Heubach et al. | 71/92 |
| 4,881,966 | 11/1989 | Nyffeler et al. | 71/94 |
| 4,891,057 | 1/1990 | Sohn et al. | 71/72 |
| 4,902,340 | 2/1990 | Hubele | 71/94 |
| 4,925,478 | 5/1990 | Sohn et al. | |

FOREIGN PATENT DOCUMENTS

| | | |
|---|---|---|
| 34951/89 | 11/1989 | Austria . |
| 0094349 | 11/1983 | European Pat. Off. . |
| 0191736 | 8/1986 | European Pat. Off. . |
| 0254222 | 1/1988 | European Pat. Off. . |
| 0269806 | 6/1988 | European Pat. Off. . |
| 0293062 | 11/1988 | European Pat. Off. . |
| 0298679 | 1/1989 | European Pat. Off. . |
| 0298680 | 1/1989 | European Pat. Off. . |
| 0333131 | 9/1989 | European Pat. Off. . |
| 0346620 | 12/1989 | European Pat. Off. . |
| 0531271 | 3/1993 | European Pat. Off. . |
| 89/1960 | 3/1989 | South Africa . |
| 90/9410 | 8/1991 | South Africa . |
| 90/9591 | 9/1991 | South Africa . |
| 0174562 | 3/1986 | WIPO . |
| WO91/05469 | 5/1991 | WIPO . |
| WO91/07874 | 6/1991 | WIPO . |
| WO91/08202 | 6/1991 | WIPO . |

OTHER PUBLICATIONS

Chemical Abstracts, vol. 108, No. 17, Columbus, Ohio, US, abstract No. 145356d, Z. Ekler et al., "Synergism and antagonism of herbicides with monoxygenase inhibitors", & Proc. Br. Crop Prot. Conf.—Weeds, Bd. 3, 1987.

Search Report for EP 92 12 1984.

Weed Technology, vol. 4, pp. 731–738. Wilson et al. 1990.

*Primary Examiner*—S. Mark Clardy
*Attorney, Agent, or Firm*—Curtis, Morris & Safford

[57] ABSTRACT

Herbicide/safener combinations of
A) herbicides selected from the group of the 2-acylated 1,3-dicarbonyl compounds or salts thereof, and
B) safeners B1 and/or B2

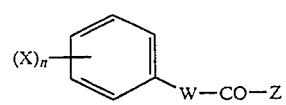

(B1)

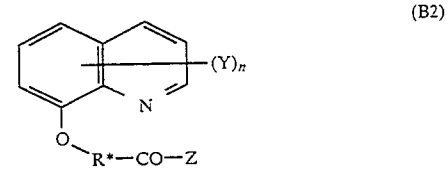

(B2)

as they are defined in claim 1, are suitable for controlling harmful plants in crops such as cereals, maize and rice.

15 Claims, No Drawings

COMBINATIONS OF BENZOYL CYCLOHEXANEDIONE HERBICIDES AND CROP-PROTECTING SUBSTANCES

The invention relates to the technical field of the crop protection agents, in particular active substance/antidote combinations, which are outstandingly suitable for being used against harmful plants in crops of useful plants.

Some more recent herbicidal active substances have very good activities and selectivities and can be used against a broad spectrum of various broad-leaf weeds and/or grass weeds in specific crop stands such as soya beans, maize, rice or cereals. However, other crop plants are harmed by these herbicides, so that they cannot be used in such crops at all, or only at low application rates which do not guarantee the best possible, broad herbicidal activity.

Examples of such herbicides whose application is limited are some herbicides from the group of the 2-acylated cyclic 1,3-dicarbonyl compounds of the formula A or salts thereof,

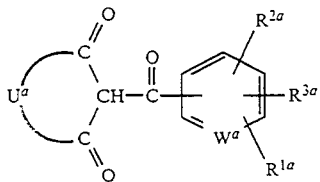

(A)

in which

R$^{1a}$ and R$^{3a}$ independently of one another are hydrogen, halogen, alkyl, alkoxy, haloalkyl, haloalkoxy, CN, NO$_2$, S(O)$_m$R$^{11a}$, NR$^{12a}$R$^{13a}$, NR$^{14a}$C(O)R$^{15a}$, C(O)R$^{16a}$ or OCH$_2$CH$_2$OR$^{21a}$, R$^{2a}$ is halogen, CN, NO$_2$, alkyl, alkoxy, haloalkyl or haloalkoxy, S(O)$_p$R$^{10a}$, —O—S(O)$_2$R$^{10a}$, N(R$^{20a}$)—S(O)$_2$R$^{19a}$, W$^a$ is nitrogen or CH, R$^{10a}$ is alkyl, haloalkyl or alkoxy, R$^{11a}$ is alkyl, haloalkyl, phenyl or benzyl, the last two radicals being unsubstituted or substituted on the phenyl ring, or is NR$^{17a}$R$^{18a}$, R$^{12a}$, R$^{13a}$ independently of one another are hydrogen or alkyl, R$^{14a}$ is alkyl or hydrogen, R$^{15a}$ is alkyl or hydrogen, R$^{16a}$ is hydrogen, alkyl, haloalkyl or alkoxy, R$^{17a}$ and R$^{18a}$ independently of one another are hydrogen or alkyl, R$^{19a}$ and R$^{20a}$ independently of one another are alkyl or haloalkyl, R$^{21a}$ is hydrogen or alkyl, p is zero or one and U$^a$ and the group of the formula —CO—CH—CO— bonded to it together form a ring which has 5 to 6 ring members and which is carbocyclic or heterocyclic and, apart from the two oxo groups, not substituted or further substituted.

The herbicides of the formula A or the salts thereof are inhibitors of chlorophyll or carotinoid biosynthesis in plants. After plants have been treated with such active substances, the leaves show pale areas and white chloroses which gradually extend over the entire plant and destroy it (compare Weed Technology, 1990, Vol. 4, pages 731–738; WSSA Abstracts, Vol. 31, 1991, Meeting WSSA Feb. 4–7, Abstr. 33, page 11; DE-A-4107141).

Many herbicides of the formula A or salts thereof (compounds A) cannot be employed selectively, or not selectively at sufficient high dosage rates, in crops of cereals and/or in maize because these crop plants are damaged, at least at the desired dosage rates required for a broad herbicidal activity against broad-leaf weeds and grass weeds.

In the case of compounds A, the use of herbicidal antidotes (safeners) such as, for example, chloro- or bromo-acetamides, dichloroacetamides, thiazolidines, N-phenylcarbamates, N-phenylsulfonylcarbamates, and 1,8-naphthalenedicarboxylic anhydride has already been disclosed. (cf. EP-A-2,986,79 and EP-A-2,986,80). In some cases, the crop plant such as, for example, wheat, can be protected against the harmful activity of the herbicide (cf. EP-A-2,986,80, Tab. X, P 48).

Entirely unexpectedly, experimental work has now revealed that crop plants such as, for example, wheat, barley, maize or rice, can be protected against undesired damage caused by herbicides of the formula A or salts thereof (compounds A) when they are applied together with certain compounds (B) which act as herbicidal antidotes or safeners.

The invention therefore relates to herbicidal compositions which comprise an effective amount of A) one or more herbicides selected from the group comprising the 2-acylated, 1,3-dicarbonyl compounds of the abovementioned formula A or salts thereof, as well as B) one or more compounds of the formula B1 and B2,

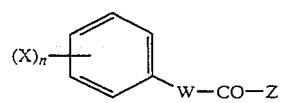

(B1)

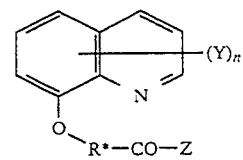

(B2)

in which

X is hydrogen, halogen, C$_1$–C$_4$-alkyl, C$_1$–C$_4$-alkoxy, nitro or C$_1$–C$_4$-haloalkyl, Y is halogen, C$_1$–C$_4$-alkyl, C$_1$–C$_4$alkoxy, nitro or C$_1$–C$_4$-haloalkyl, R* is a C$_1$–C$_2$-alkylene chain which can additionally be substituted by one or two C$_1$–C$_4$-alkyl radicals, and is preferably —CH$_2$—, Z is OR$^1$, SR$^1$ or NR$^1$R, preferably a radical of the formula OR$^1$, NHR$^1$ or N(CH$_3$)R$^1$, in particular of the formula OR$^1$, R independently of R$^1$ is hydrogen, C$_1$–C$_6$-alkyl, C$_1$–C$_6$-alkoxy or phenyl or substituted phenyl or R and R$^1$ together with the nitrogen atom bonded to them are a saturated or unsaturated 3- to 7-membered heterocycle which has at least one nitrogen atom and up to 3 hetero atoms and which is unsubstituted or substituted by radicals selected from the group comprising C$_1$–C$_4$-alkyl, C$_1$–C$_4$-alkoxy, phenyl or substituted phenyl, $R^1$ independently of R is hydrogen, $C_1$–$C_{18}$-alkyl, $C_3$–$C_{12}$-cycloalkyl, $C_2$–$C_8$-alkenyl or $C_2$–$C_8$-alkynyl, where each of the above carbon-containing radicals independently of one another is unsubstituted or mono- or polysubstituted by radicals selected from the group comprising halogen, hydroxyl, $C_1$–$C_8$-alkoxy, $C_1$–$C_8$-alkylthio, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, cyano, mono- and di-($C_1$–$C_4$-alkyl)-amino, ($C_1$–$C_8$-alkoxy)-carbonyl, ($C_2$–$C_8$-alkenyloxy)-carbonyl, ($C_1$–$C_8$-alkylthio)-carbonyl, ($C_2$–$C_8$-alkynyloxy)-carbonyl, ($C_1$–$C_8$-alkyl)-carbonyl, ($C_2$–$C_8$-alkenyl)-carbonyl, ($C_2$–$C_8$-alkynyl)-carbonyl, 1-(hydroxyimino)-$C_1$–$C_6$-alkyl, 1-($C_1$–$C_4$-alkylimino)-$C_1$–$C_6$-alkyl, 1-($C_1$–$C_4$-alkoxyimino)-$C_1$–$C_6$-alkyl, ($C_1$–$C_8$-alkyl)-carbonylamino, ($C_2$–$C_8$-alkenyl)-carbonylamino, ($C_2$–$C_8$-alkynyl)-carbonylamino, aminocarbonyl, ($C_1$–$C_8$-alkyl)-aminocarbonyl, di-($C_1$–$C_6$-alkyl)-aminocarbonyl, ($C_2$–$C_6$-alkenyl)-aminocarbonyl, ($C_2$–$C_6$-alkynyl)-aminocarbonyl, ($C_1$–$C_8$-alkoxy)-carbonylamino, ($C_1$–$C_8$-alkyl)-aminocarbonylamino, $C_1$–$C_6$-alkylcarbonyloxy, which is unsubstituted or substituted by halogen, $NO_2$, $C_1$–$C_4$-alkoxy or optionally substituted phenyl, furthermore comprising ($C_2$–$C_6$-alkenyl)-carbonyloxy, ($C_2$–$C_6$-alkynyl)-carbonyloxy, $C_1$–$C_8$-alkylsulfonyl, phenyl, phenyl-$C_1$–$C_6$-alkoxy, phenyl-($C_1$–$C_6$-alkoxy)-carbonyl, phenoxy, phenoxy-$C_1$–$C_6$-alkoxy, phenoxy-($C_1$–$C_6$-alkoxy)-carbonyl, phenylcarbonyloxy, phenylcarbonylamino, phenyl-($C_1$–$C_6$-alkyl)-carbonylamino, the 9 last-mentioned radicals being unsubstituted or mono- or poly-substituted in the phenyl ring by radicals selected from halogen, $C_1$–$C_4$-alkyl, $C_1$–$C_4$-alkoxy, $C_1$–$C_4$-haloalkyl, $C_1$–$C$-haloalkoxy and nitro and furthermore comprising radicals of the formulae $-SiR'_3$, $-OSiR'_3$, $(R')_3Si-C_1-C_6-$Alkoxy, $-CO-O-NR'_2$, $-O-N=CR'_2$, $-N=CR'_2$, $-O-NR'_2$, $-CH(OR')_2$ and $-O-(CH_2)_m-CH(OR')_2$, in which the R' in the abovementioned formulae independently of one another are halogen, $C_1$–$C_4$-alkyl or phenyl which is unsubstituted or mono- or polysubstituted by radicals selected from halogen, $C_1$–$C_4$-alkyl, $C_1$–$C_4$-alkoxy, $C_1$–$C_4$-haloalkyl, $C_1$–$C_4$-haloalkoxy and nitro, or the R', as a pair, are a $C_2$–$C_6$-alkylene chain and m is 0 to 6, and furthermore comprising an alkoxy radical of the formula $R''O-CR'''(OR'')-C_1-C_6$-alkoxy, in which the R'' independently of one another are $C_1$–$C_4$-alkyl or together are a $C_1$–$C_6$-alkylene group and R''' is hydrogen or $C_1$–$C_4$-alkyl, n is an integer from 1 to 5, preferably 1 to 3, and W is a divalent heterocyclic radical having 5 ring atoms, of the formula W1 to W4,

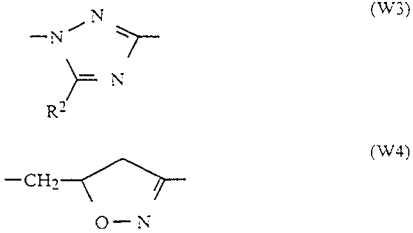

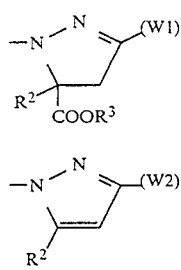

in which $R^2$ is hydrogen, $C_1$–$C_8$-alkyl, $C_1$–$C_8$-haloalkyl, $C_3$–$C_{12}$-cycloalkyl or optionally substituted phenyl and $R^3$ is hydrogen, $C_1$–$C_8$-alkyl, $C_1$–$C_8$-haloalkyl, ($C_1$–$C_4$-alkoxy)-$C_1$–$C_4$-alkyl, $C_1$–$C_6$-hydroxyalkyl, $C_3$–$C_{12}$-cycloalkyl or tri-($C_1$–$C_4$-alkyl)-silyl.

Particularly interesting herbicidal compositions according to the invention are those in which, in compounds of the formulae B1 and B2, $R^1$ is hydrogen, $C_1$–$C_{12}$-alkyl, $C_3$–$C_7$-cycloalkyl, $C_2$–$C_8$-alkenyl or $C_2$–$C_8$-alkynyl, where each of the abovementioned carbon-containing radicals independently of one another is unsubstituted or mono- or polysubstituted by halogen or mono- or disubstituted, preferably up to monosubstituted, by radicals selected from the group comprising hydroxyl, $C_1$–$C_4$-alkoxy, $C_1$–$C_4$-alkylthio, $C_2$–$C_4$-alkenyloxy, $C_2$–$C_4$-alkynyloxy, mono and di-($C_2$–$C_2$-alkyl)-amino, ($C_1$–$C_4$-alkoxy)-carbonyl, ($C_2$–$C_4$-alkenyloxy)-carbonyl, ($C_2$–$C_4$-alkynyloxy)-carbonyl, ($C_1$–$C_4$-alkyl-carbonyl, ($C_2$–$C_4$-alkenyl)-carbonyl, ($C_2$–$C_4$-alkynyl)-carbonyl, 1-(hydroxyimino)-$C_1$–$C_4$-alkyl, 1-($C_1$–$C_4$-alkylimino-$C_1$–$C_4$-alkyl, 1-($C_1$–$C_4$-alkoxy imino)-$C_1$–$C_4$-alkyl, $C_1$–$C_4$-alkylsulfonyl, phenyl, phenyl-$C_1$–$C_4$-alkoxy, phenyl-($C_1$–$C_4$-alkoxy)-carbonyl, phenoxy, phenoxy-$C_1$–$C_4$-alkoxy, phenoxy-($C_1$–$C_4$-alkoxy)-carbonyl, where the 6 last-mentioned radicals are unsubstituted or mono- or polysubstituted in the phenyl ring by radicals selected from the group comprising halogen, $C_1$–$C_2$-alkyl, $C_1$–$C_2$-alkoxy, $C_1$–$C_2$-haloalkyl, $C_1$–$C_2$-haloalkoxy and nitro, and radicals of the formulae $-SiR'_3$, $-O-N=CR'_2$, $-N=CR'_2$ and $-O-NR'_2$, in which R' in the abovementioned formulae independently of one another are hydrogen, $C_1$–$C_2$-alkyl or phenyl which is unsubstituted or mono- or polysubstituted by radicals selected from the group comprising halogen, $C_1$–$C_2$-alkyl, $C_1$–$C_2$-alkoxy, $C_1$–$C_2$-haloalkyl, $C_1$–$C_2$-haloalkoxy and nitro, or, in pairs, are a $C_4$–$C_5$-alkylene chain.

Other particularly interesting herbicidal compositions according to the invention are those in which, in the compounds of the formulae B1 and B2, X is hydrogen, halogen, methyl, ethyl, methoxy, ethoxy or $C_1$–$C_2$-haloalkyl, preferably hydrogen, halogen or $C_1$–$C_2$-haloalkyl, and Y is halogen, methyl, ethyl, methoxy, ethoxy, or $C_1$–$C_2$-haloalkyl, preferably hydrogen, halogen or $C_1$–$C_2$-haloalkyl.

Preferred herbicidal compositions according to the invention are those in which, in the compounds of the formula B1, X is hydrogen, halogen, nitro or $C_1$–$C_4$-haloalkyl, n is a number from 1 to 3, Z is a radical of the formula $OR^1$, $R^1$ is hydrogen, $C_1$–$C_8$-alkyl or $C_3$–$C_7$-cycloalkyl, where each of the abovementioned carbon-containing radicals independently of one another is unsubstituted or mono- or polysubstituted by radicals selected from the group comprising halogen or monosubstituted or disubstituted, preferably unsubstituted or monosubstituted, by radicals selected from the group comprising hydroxyl, $C_1$–$C_4$-alkoxy, ($C_1$–$C_4$-alkoxy)-carbonyl, $C_2$–$C_6$-alkenyloxy-carbonyl, ($C_2$–$C_6$-alkynyloxy)carbonyl, 1-(hydroxyimino)-$C_1$–$C_4$-alkyl, 1-($C_1$–$C_4$-alkylimino)-$C_1$–$C_4$-alkyl, 1-($C_1$–$C_4$-alkoxyimino)-$C_1$–$C_4$-alkyl, and radicals of the formulae $-SiR'_3$, $-O-N=CR'_2$, $-N=CR'_2$- and $-O-NR'_2$, in which the $R'$ in the abovementioned formulae independently of one another are hydrogen or $C_1$–$C_4$-alkyl or, in pairs, are $C_4$–$C_5$-alkylene chain, $R^2$ is hydrogen, $C_1$–$C_8$-alkyl, $C_1$–$C_6$-haloalkyl, $C_3$–$C_7$-cycloalkyl or phenyl and $R^3$ is hydrogen, $C_1$–$C_8$-alkyl, $C_1$–$C_8$-haloalkyl, ($C_1$–$C_4$-alkoxy) -$C_1$–$C_4$-alkyl, $C_1$–$C_6$-hydroxyalkyl, $C_3$–$C_7$-cycloalkyl or tri-($C_1$–$C_4$-alkyl)-silyl.

Other preferred herbicidal compositions according to the invention are those in which, in the compounds of the formula B2, Y is halogen or $C_1$–$C_4$-haloalkyl and n is a number from 1 to 3, preferably $(Y)_n = 5-Cl$, Z is a radical of formula $OR^1$, R* is $CH_2$ and $R^1$ is hydrogen, $C_1$–$C_8$-alkyl, $C_1$–$C_8$-haloalkyl or ($C_1$–$C_4$-alkoxy)-$C_1$–$C_4$-alkyl, 1-(hydroxyimino)-$C_1$–$C_4$-alkyl, 1-($C_1$–$C_4$-alkylimino)-$C_1$–$C_3$-alkyl, 1-($C_1$–$C_2$-alkoxyimino)-$C_1$–$C_3$-alkyl, preferably $C_1$–$C_8$-alkyl.

Particularly preferred herbicidal compositions according to the invention are those which contain compounds of the formula B1 in which W is W1, X is H, halogen or $C_1$–$C_2$-haloalkyl and n is 1–3, in particular $(X)_n = 2,4$-$Cl_2$, Z is a radical of the formula $OR^1$, $R^1$ is hydrogen, $C_1$–$C_8$-alkyl, $C_1$–$C_4$-haloalkyl, $C_1$–$C_4$-hydroxyalkyl, $C_3$–$C_7$-cycloalkyl, ($C_1$–$C_4$-alkoxy)-$C_1$–$C_4$-alkyl, tri-($C_1$–$C_2$-alkyl)-silyl, preferably $C_1$–$C_4$-alkyl, $R^2$ is hydrogen, $C_1$–$C_8$-alkyl, $C_1$–$C_4$-haloalkyl or $C_3$–$C_7$-cycloalkyl, preferably hydrogen or $C_1$–$C_4$-alkyl, and $R^3$ is hydrogen, $C_1$–$C_8$-alkyl, $C_1$–$C_4$-haloalkyl, $C_1$–$C_4$-hydroxyalkyl, $C_3$–$C_7$-cycloalkyl, ($C_1$–$C_4$-alkoxy)-$C_1$–$C_4$-alkyl or tri-($C_1$–$C_2$-alkyl)-silyl, preferably H or $C_1$–$C_4$-alkyl.

Other particularly preferred herbicidal compositions according to the invention are those which contain compounds of the formula B1 in which W is W2, X is H, halogen or $C_1$–$C_2$-haloalkyl and n is 1–3, in particular $(X)_n = 2,4$-$Cl_2$, Z is a radical of the formula $OR^1$, $R^1$ is hydrogen, $C_1$–$C_8$-alkyl, $C_1$–$C_4$-haloalkyl, $C_1$–$C_4$-hydroxyalkyl, $C_3$–$C_7$-cycloalkyl, ($C_1$–$C_4$-alkoxy)-$C_1$–$C_4$-alkyl, tri-($C_1$–$C_2$-alkyl)-silyl, preferably $C_1$–$C_4$-alkyl, and $R^2$ is hydrogen, $C_1$–$C_8$-alkyl, $C_1$–$C_4$-haloalkyl or $C_3$–$C_7$-cycloalkyl, or phenyl, preferably hydrogen or $C_1$–$C_4$-alkyl.

Other particularly preferred herbicidal compositions according to the invention are those which contain compounds of the formula B1, in which W is W3, X is H, halogen or $C_1$–$C_2$-haloalkyl and n is 1–3, in particular $(X)_n = 2,4$-$Cl_2$, Z is a radical of the formula $OR^1$, $R^1$ is hydrogen, $C_1$–$C_8$-alkyl, $C_1$–$C_4$-haloalkyl, $C_1$–$C_4$-hydroxyalkyl, $C_3$–$C_7$-cycloalkyl, ($C_1$–$C_4$-alkoxy)-$C_1$–$C_4$-alkyl, tri-($C_1$–$C_2$-alkyl)-silyl, preferably $C_1$–$C_4$-alkyl, and $R^2$ is $C_1$–$C_8$-alkyl or $C_1$–$C_4$-haloalkyl preferably $C_1$-haloalkyl.

Other particularly preferred herbicidal compositions according to the invention are those which contain compounds of the formula B1 in which W is W4, X is H, hydrogen, halogen, nitro, $C_1$–$C_4$alkyl, $C_1$–$C_2$-haloalkyl, preferably $CF_3$, or $C_1$–$C_4$-alkoxy, n is 1 to 3, Z is a radical of the formula $OR^1$, $R^1$ is hydrogen, $C_1$–$C_4$-alkyl, or ($C_1$–$C_4$-alkoxy)-carbonyl -$C_1$–$C_4$-alkyl, preferably a radical of the formula ($C_1$–$C_4$-alkoxy)-CO-$CH_2$-, ($C_1$–$C_4$-alkoxy)-CO-C($CH_3$)H-, HO-CO-$CH_2$ or HO-CO-C($CH_3$)H.

In the formulae, alkyl, alkenyl and alkynyl are straight-chain or branched; the same applies analogously to substituted alkyl, alkenyl and alkynyl radicals such as haloalkyl, hydroxyalkyl, alkoxycarbonyl and the like; alkyl is, for example, methyl, ethyl, n- and i-propyl, n-, i-, t- and 2-butyl, the pentyl radicals, the hexyl radicals such as n-hexyl, i-hexyl and 1,3- dimethylbutyl, the heptyl radicals such as n-heptyl, 1-methylhexyl and 1,4-dimethylpentyl; alkenyl is, for example, allyl, 1-methylprop-2-en-1-yl, but-2-en-1-yl, but-3-en-1-yl, 1-methyl-but-3-ene and 1-methyl-but-2-ene; alkynyl is, for example, propargyl, but-2-yn-1-yl, but-3-yn-1-yl, 1-methyl-but-3-yne; halogen is fluorine, chlorine, bromine or iodine, preferably fluorine, chlorine or bromine, in particular fluorine or chlorine; haloalkyl, haloalkenyl and haloalkynyl are halogen-substituted alkyl, alkenyl or alkynyl, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $CF_3CH_2O$; optionally substituted phenyl is phenyl or substituted phenyl; substituted phenyl is phenyl which is mono- or polysubstituted by radicals selected from the group comprising halogen, $C_1$–$C_4$-alkyl, $C_1$–$C_4$-alkoxy, $C_1$–$C_4$-haloalkyl, $C_1$–$C_4$-haloalkoxy and nitro, for example o-, m- and p-tolyl, the dimethyl phenyl radicals, 2-, 3- and 4-chlorophenyl 2-, 3- and 4-trifluoro- and -trichlorophenyl, 2,4-, 3,5-, 2,5- and 2,3-dichlorophenyl, o-, m- and p-methoxyphenyl.

The compounds of the formula B1 are disclosed in EP-A-0,333,131 (ZA-89/1960), EP-A-0,269,806 (US-A-4,891,057), EP-A-0,346,620 (AU-A-89/34951), WO-91/08202 (International Patent Application PCT/EP 90/01966) and WO-91/07874) International Patent Application No. PCT/EP 90/02020) and literature cited therein, or they can be prepared by, or analogously to, the processes described therein. The compounds of the formula B2 are disclosed in EP-A-94349 (US-A4,902,340), EP-A-0,191,736 (US-A-4,881,966) and from German Patent Application P 4041121.4 and the literature cited therein, or they can be prepared by, or analogously to, the processes described therein.

Suitable according to the invention as compounds A are 2-acylated cyclic 1,3-dicarbonyl compounds or salts thereof which can only be employed favorably in cereal crops, rice and/or maize in combination with compounds of type B since they inflict too much damage on the crop plants on their own without safener of the type B. Examples of interesting compounds of the abovementioned formula A of salts thereof, which can be used according to the invention, are those in which $R^{1a}$ and $R^{3a}$ independently of one another are hydrogen, halogen, $(C_1-C_4)$-alkyl, $(C_1-C_4)$-alkoxy, $(C_1-C_4)$-haloalkyl, $(C_1-C_3)$-haloalkoxy, CN, NO$_2$, $S(O)_mR^{11a}$, $NR^{12a}R^{13a}$, $NR^{14a}C(O)R^{15a}$, $C(O)R^{16a}$, $OCH_2CH_2OR^{21a}$, $R^{2a}$ is halogen, CN, NO$_2$, $(C_1-C_4)$-alkyl, $(C_1-C_4)$-alkoxy, $(C_1-C_4)$-haloalkyl, $(C_1-C_4)$-haloalkoxy, $S(O)_pR^{10a}$, $-O-S(O)_2R^{10a}$, $N(R^{20a})-S(O)_2R^{19a}$, $W^a$ is nitrogen or CH, $U^a$ is a divalent group of the formula $-X^a-(Y^a)_n-Z^a-$, $X^a$ is $CR^{4a}R^{5a}$ or $N-R^{22a}$, $Y^a$ is $CR^{6a}R^{7a}$, carbonyl, oxygen, sulfur, $N-R^{23a}$ or $C=CH_2$, $Z^a$ is $CR^{8a}R^{9a}$, $N-R^{24a}$, oxygen or sulfur, $R^{4a}$, $R^{5a}$, $R^{6a}$, $R^{7a}$, $R^{8a}$ and $R^{9a}$ independently of one another are hydrogen, halogen, hydroxyl, $(C_1-C_4)$-alkyl, $(C_1-C_4)$-alkylthio, $[(C_1-C_4)$-alkoxy]-carbonyl, $(C_3-C_6)$-cycloalkyl or phenyl, the 5 last-mentioned hydrocarbon-containing radicals being unsubstituted or substituted by one or more halogen atoms, $R^{10a}$ is $(C_1-C_4)$-alkyl, $(C_1-C_4)$-haloalkyl or $(C_1-C_4)$-alkoxy $R^{11a}$ is $(C_1-C_4)$-alkyl, $(C_1-C_4)$-haloalkyl, phenyl, substituted phenyl, benzyl or $NR^{17a}R^{18a}$, $R^{12a}$, $R^{13a}$ independently of one another are hydrogen or $(C_1-C_4)$-alkyl, $R^{14a}$ is hydrogen or $(C_1-C_4)$-alkyl, $R^{15a}$ is hydrogen or $(C_1-C_4)$-alkyl, $R^{16a}$ is hydrogen, $(C_1-C_4)$-alkyl, $(C_1-C_4)$-haloalkyl or $(C_1-C_4)$-alkoxy, $R^{17a}$ and $R^{18a}$ independently of one another are hydrogen or $(C_1-C_4)$-alkyl, $R^{19a}$ and $R^{20a}$ independently of one another are $(C_1-C_4)$-alkyl or $(C_1-C_4)$-haloalkyl, $R^{21a}$, $R^{22a}$, $R^{23a}$ and $R^{24a}$ independently of one another are hydrogen or $(C_1-C_4)$-alkyl and m, n and p independently of one another are zero or one.

Preferred compounds of the abovementioned formulae or salts thereof, which can be employed according to the invention, are those in which $R^{1a}$ and $R^{3a}$ independently of one another are hydrogen, fluorine, chlorine, bromine, iodine, cyano, nitro, $-SO_2R^{11a}$, $NR^{12a}R^{13a}$, $-N(CH_3)-C(O)R^{15a}$, $[(C_1-C_4)$-alkoxy]-carbonyl, $(C_1-C_2)$-alkyl, $(C_1-C_2)$-alkoxy, $OCH_2CH_2OR^{21a}$, $(C_1-C_2)$-haloalkyl, $(C_1-C_2)$-haloalkoxy or $(C_1-C_2)$-alkylthio, $R^{2a}$ is fluorine, chlorine, bromine, iodine, cyano, nitro, $S(O)_pR^{10a}$, $(C_1-C_3)$-alkyl, $(C_1-C_2)$-alkoxy, $(C_1-C_3)$-haloalkyl or $(C_1-C_2)$-haloalkoxy, $U^a$ is a divalent group of the formula $-X^a-(Y^a)_n-Z^a-$, $W^a$ is nitrogen or CH, $X^a$ is $CR^{4a}R^{5a}$ or $N-R^{22a}$, $Y^a$ is $CR^{6a}R^{7a}$, carbonyl, oxygen, sulfur, $N-R^{23a}$ or $C=CH_2$, $Z^a$ is $CR^{8a}R^{9a}$, $N-R^{24a}$, oxygen or sulfur, $R^{4a}$, $R^{5a}$, $R^{6a}$, $R^{7a}$, $R^{8a}$ and $R^{9a}$ independently of one another are hydrogen, fluorine, chlorine, bromine, hydroxyl $(C_1-C_3)$-alkyl, $(C_4-C_6)$-cycloalkyl, $(C_1-C_2)$-alkylthio and phenyl, the 4 last-mentioned hydrocarbon-containing radicals being unsubstituted or substituted by one or more halogen atoms and $R^{21a}$, $R^{22a}$, $R^{23a}$ and $R^{24a}$ independently of one another are $(C_1-C_4)$-alkyl, and $R^{10a}$, $R^{11a}$, $R^{12a}$, $R^{13a}$, $R^{15a}$, p and n are as defined above.

Particularly preferred compounds of the formula A or salts thereof are those in which $R^{1a}$ and $R^{3a}$ independently of one another are hydrogen, fluorine, chlorine, bromine, methoxy, ethoxy, methyl, trifluoromethoxy, difluoromethoxy, $OCH_2CH_2OCH_3$, nitro, trifluoromethyl, methylthio, $-SO_2CH_3$, $SO_2CH_2CH_3$, $SO_2CH_2CH_2CH_3$, $SO_2CH_2Cl$, $-N(CH_3)_2$, $OCH_2CH_2Cl$, $OCH_2CF_3$, $SO_2N(CH_3)_2$, ethyl, n-propyl or $[(C_1-C_4)$-alkoxy]-carbonyl, $R^{2a}$ is fluorine, chlorine, bromine, iodine, cyano, nitro, $S(O)_pR^{10a}$, $(C_1-C_3)$-alkyl, $(C_1-C_2)$-alkoxy, $(C_1-C_3)$-haloalkyl or $(C_1-C_2)$-haloalkoxy, $R^{4a}$, $R^{5a}$, $R^{6a}$ $R^{7a}$, $R^{8a}$ and $R^{9a}$ independently of one another are hydrogen, methyl, ethyl, propyl, isopropyl, cyclopentyl, hydroxyl, methylthio, fluorine, chlorine, bromine and phenyl which is optionally substituted by one or more halogen atoms, and p is two Tables 1 to 5 below give examples of the abovementioned herbicidal 2-acyl-1,3-dicarbonyl compounds of the formula A.

TABLE 1

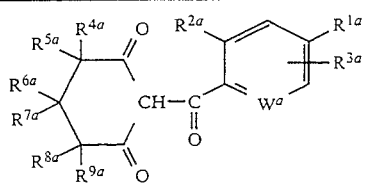

| Ex. | $R^{1a}$ | $R^{2a}$ | $R^{3a}$ | $R^{4a}$ | $R^{5a}$ | $R^{6a}$ | $R^{7a}$ | $R^{8a}$ | $R^{9a}$ | $W^a$ |
|---|---|---|---|---|---|---|---|---|---|---|
| 1 | Cl | NO$_2$ | H | H | H | H | H | H | H | CH |
| 2 | H | NO$_2$ | H | H | H | CH$_3$ | CH$_3$ | H | H | C(CH$_3$) |
| 3 | SO$_2$C$_2$H$_5$ | Cl | H | H | H | H | H | H | H | CH |
| 4 | SO$_2$C$_2$H$_5$ | Cl | H | H | H | CH$_3$ | CH$_3$ | H | H | CH |
| 5 | NO$_2$ | Cl | H | CH$_3$ | CH$_3$ | H | H | H | H | CH |
| 6 | Cl | NO$_2$ | H | CH$_3$ | CH$_3$ | H | H | H | H | CH |
| 7 | Cl | NO$_2$ | H | H | H | CH$_3$ | CH$_3$ | H | h | CH |
| 8 | H | H | 3-CF$_3$O | H | H | CH$_3$ | CH$_3$ | H | H | CH |
| 9 | F | Cl | H | H | H | CH$_3$ | CH$_3$ | H | H | CH |

TABLE 1-continued

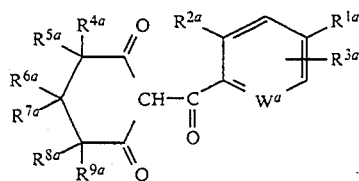

| Ex. | $R^{1a}$ | $R^{2a}$ | $R^{3a}$ | $R^{4a}$ | $R^{5a}$ | $R^{6a}$ | $R^{7a}$ | $R^{8a}$ | $R^{9a}$ | $W^a$ |
|---|---|---|---|---|---|---|---|---|---|---|
| 10 | SO₃CH₃ | Cl | H | H | i-C₃H₇ | H | H | H | H | CH |
| 11 | H | NO₂ | H | CH₃ | CH₃ | H | H | H | H | CH |
| 12 | H | NO₂ | H | H | CH₃ | H | H | CH₃ | CH₃ | CH |
| 13 | Cl | NO₂ | H | CH₃ | H | H | H | CH₃ | CH₃ | CH |
| 14 | NO₂ | Cl | H | CH₃ | CH₃ | H | H | CH₃ | H | CH |
| 15 | Cl | Cl | H | i-C₃H₇ | H | H | H | H | H | CH |
| 16 | SO₂CH₃ | Cl | 3-OC₂H₅ | H | H | H | H | H | H | CH |
| 17 | H | CN | H | CH₃ | CH₃ | H | H | H | H | CH |
| 18 | CF₃ | NO₂ | H | H | H | H | H | H | H | CH |
| 19 | SO₂CH₃ | NO₂ | H | CH₃ | CH₃ | H | H | H | H | CH |
| 20 | SO₂CH₃ | Cl | H | H | H | H | H | H | H | CH |
| 21 | SO₂CH₂Cl | NO₂ | H | CH₃ | CH₃ | H | H | H | H | CH |
| 22 | CF₃ | Cl | H | H | H | H | H | H | H | N |
| 23 | SO₂CH₃ | Cl | H | H | H | H | H | H | H | N |
| 24 | CF₃ | NO₂ | H | CH₃ | CH₃ | H | OH | CH₃ | CH₃ | CH |
| 25 | H | SO₂CH₃ | H | CH₃ | CH₃ | H | H | CH₃ | H | CH |
| 26 | SO₂CH₂CH₂CH₃ | SCH₃ | H | H | H | H | H | H | H | CH |
| 27 | SO₂CH₃ | CH₃ | H | CH₃ | CH₃ | H | H | H | CH₃ | CH |
| 28 | SO₂CH₂CH₃ | CH₃ | 3-Cl | H | H | H | H | H | H | CH |
| 29 | SCH₂CH₃ | CF₃ | H | H | H | H | H | H | H | CH |
| 30 | CF₃ | CF₃ | H | CH₃ | CH₃ | H | H | H | H | CH |
| 31 | H | NO₂ | H | H | H | H | H | CH₃ | SCH₃ | CH |
| 32 | SO₂CH₃ | Cl | H | H | H | H | CH₃ | 2-F—C₆H₄ | H | CH |
| 33 | Cl | NO₂ | H | H | H | H | H | H | 2-F—C₆H₄ | CH |
| 34 | SO₂CH₃ | Cl | H | —C₆H₅ | H | H | H | H | H | CH |
| 35 | SO₂CH₃ | Cl | H | CH₃ | CH₃ | C₆H₅ | H | H | H | CH |
| 36 | Cl | NO₂ | H | H | H | H | C₆H₅ | H | H | CH |
| 37 | SO₂CH₃ | Cl | H | SCH₃ | H | H | H | H | H | CH |
| 38 | Cl | NO₂ | H | H | H | H | H | H | SCH₃ | CH |
| 39 | SO₂CH₃ | Cl | H | H | Br | H | H | H | H | CH |
| 40 | H | NO₂ | H | Br | H | H | H | CH₃ | CH₃ | CH |
| 41 | Cl | Cl | H | Cl | H | H | H | H | H | CH |
| 42 | CF₃ | NO₂ | H | F | H | CH₃ | CH₃ | H | H | CH₃-9 |
| 43 | SO₂CH₃ | Cl | H | H | H | CH₃ | CH₃ | H | H | CH |
| 44 | SO₂CH₃ | Cl | H | CH₃ | CH₃ | H | H | H | H | CH |
| 45 | SO₂CH₃ | Cl | H | CH₃ | CH₃ | H | H | H | CH₃ | CH |
| 46 | CF₃ | NO₂ | H | CH₃ | CH₃ | H | H | H | H | CH |
| 47 | OCF₂H | NO₂ | H | H | H | H | H | H | H | CH |
| 48 | OCF₂H | NO₂ | H | CH₃ | CH₃ | H | H | H | H | CH |
| 49 | SO₂CH₂CH₂CH₃ | Cl | 3-OCH₂CH₂OCH₃ | H | H | H | H | H | H | CH |

TABLE 2

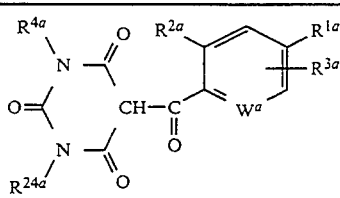

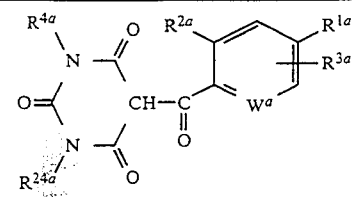

| Ex. | $R^{1a}$ | $R^{2a}$ | $R^{3a}$ | $R^{22a}$ | $R^{24a}$ |
|---|---|---|---|---|---|
| 1 | Cl | Cl | H | CH₃ | CH₃ |
| 2 | H | NO₂ | H | CH₃ | CH₃ |
| 3 | SO₂C₂H₅ | Cl | 3-CH₂CH₂CH₃ | CH₃ | CH₃ |

TABLE 3

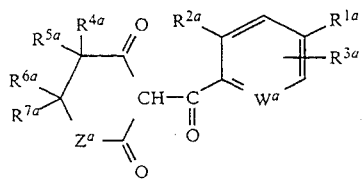

| Ex. | $R^{1a}$ | $R^{2a}$ | $R^{3a}$ | $R^{4a}$ | $R^{5a}$ | $R^{6a}$ | $R^{7a}$ | $Z^a$ |
|---|---|---|---|---|---|---|---|---|
| 1 | Cl | Cl | H | H | H | | $=CH_2$ | O |
| 2 | H | $NO_2$ | H | $CH_3$ | H | H | H | O |
| 3 | Cl | $NO_2$ | H | $CH_3$ | H | $CH_3$ | H | O |
| 4 | $SO_2CH_3$ | Cl | H | H | $CH_3$ | H | $CH_3$ | S |
| 5 | Cl | $NO_2$ | H | H | H | H | H | $N-CH_2CH_2CH_3$ |
| 6 | $SO_2CH_3$ | Cl | H | H | H | H | H | $N-CH_2CH_2CH_3$ |
| 7 | Cl | $NO_2$ | H | H | $CH_3$ | $CH_3$ | | $N-CH_3$ |
| 8 | $SO_2CH_3$ | $NO_2$ | H | H | $CH_3$ | H | H | $N-CH_2CH_3$ |

TABLE 4

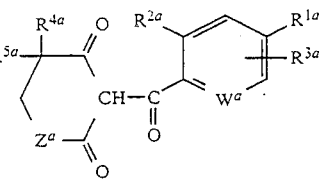

| Ex. | $R^{1a}$ | $R^{2a}$ | $R^{3a}$ | $R^{4a}$ | $R^{5a}$ | $Z^a$ |
|---|---|---|---|---|---|---|
| 1 | Cl | Cl | H | H | H | O |
| 2 | H | $NO_2$ | H | $CH_3$ | H | O |
| 3 | Cl | $NO_2$ | H | $CH_3$ | H | O |
| 4 | $SO_2CH_3$ | Cl | H | H | $CH_3$ | S |
| 5 | Cl | $NO_2$ | H | H | H | $N-CH_2CH_2CH_3$ |
| 6 | $SO_2CH_3$ | Cl | H | H | H | $N-CH_2CH_2CH_3$ |
| 7 | Cl | $NO_2$ | H | H | H | $N-CH_3$ |
| 8 | $SO_2CH_3$ | $NO_2$ | H | H | $CH_3$ | $N-CH_2CH_3$ |

TABLE 5

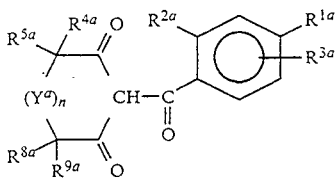

| Ex. No. | $R^{1a}$ | $R^{2a}$ | $R^{3a}$ | $R^{4a}$ | $R^{5a}$ | $R^{8a}$ | $R^{9a}$ | $Y^a$ |
|---|---|---|---|---|---|---|---|---|
| 1 | Cl | $NO_2$ | H | $CH_3$ | $CH_3$ | H | H | O |
| 2 | Cl | Cl | H | H | H | H | H | S |
| 3 | Cl | Cl | H | $CH_3$ | H | $CH_3$ | H | S |
| 4 | H | $NO_2$ | H | $CH_3$ | $CH_3$ | $CH_3$ | $CH_3$ | C=O |
| 5 | Cl | $NO_2$ | H | $CH_3$ | $CH_3$ | $CH_3$ | $CH_3$ | C=O |
| 6 | $SO_2CH_3$ | Cl | H | $CH_3$ | $CH_3$ | $CH_3$ | $CH_3$ | C=O |
| 7 | $SO_2CH_2CH_3$ | $CH_3$ | H | $CH_3$ | $CH_3$ | $CH_3$ | $CH_3$ | C=O |
| 8 | $SO_2CH_2Cl$ | $NO_2$ | H | $CH_3$ | $CH_3$ | $CH_3$ | $CH_3$ | C=O |
| 9 | $SO_2CH_2CH_3$ | Cl | $3-OCH_2CH_3$ | $CH_3$ | $CH_3$ | $CH_3$ | $CH_3$ | C=O |
| 10 | $SO_2CH_3$ | $NO_2$ | H | $CH_3$ | $CH_3$ | $CH_3$ | $CH_3$ | C=O |
| 11 | $SO_2N(CH_3)_2$ | $NO_2$ | H | $CH_3$ | $CH_3$ | $CH_3$ | $CH_3$ | C=O |
| 12 | $CF_3$ | $NO_2$ | H | $CH_3$ | $CH_3$ | $CH_3$ | $CH_3$ | C=O |
| 13 | $SO_2CH_2CH_3$ | Cl | 3-Cl | $CH_3$ | $CH_3$ | $CH_3$ | $CH_3$ | C=O |
| 14 | Br | Br | $3-OCH_2CH_2OCH_3$ | $CH_3$ | $CH_3$ | H | H | $CH_2$ |
| 15 | $SO_2CH_2CH_2CH_3$ | Br | $3-OCH_2CH_2OCH_3$ | H | H | H | H | $CH_2$ |
| 16 | $SO_2CH_2CH_3$ | Cl | $3-OCH_2CH_2OCH_3$ | H | H | H | H | $CH_2$ |

Mixtures of compounds A and the sulfonyl urea derivatives and/or imidazolinones are also suitable according to the invention for being employed together with the safeners B; the respective sulfonylureas and imidazolinones are described, for example, in European Patent Application No. 91121622.4 (EP-A-0492366).

Examples which are suitable as safeners B for the abovementioned herbicidal compounds A are the following groups of compounds of the formulae B1 and B2:
  a) Compounds of the dichlorophenylpyrazoline-3-carboxylic acid type (i.e. of the formula B1, in which W=W1 and $(X)_n=2,4-Cl_2$), preferably compounds such as
(B1-1) Ethyl 1-(2,4-dichlorophenyl)-5-(ethoxycarbonyl)-5-methyl-2-pyrazoline-3-carboxylate and related compounds as they are described in WO-91-/07874 (International Patent Application No. PCT/EP/90/02020),
  b) dichlorophenylpyrazolecarboxylic acid derivatives (i.e. of the formula B1 in which W=W2 and $(X)_n 32\ 2,4-Cl_2$), preferably compounds such as
(B1-2) ethyl 1-(2,4-dichlorophenyl)-5-methylpyrazole-3-carboxylate,
(B1-3) ethyl 1-(2,4-dichlorophenyl)-5-isopropylpyrazole-3-carboxylate,
(B1-4) ethyl 1-(2,4-dichlorophenyl)-5-(1,1-dimethylethyl) pyrazole-3-carboxylate,
(B1-5) ethyl 1-(2,4-dichlorophenyl)-5-phenylpyrazole-3-carboxylate, and related compounds as they are described in EP-A-0,333,131 and EP-A-0,269,806, c) compounds of the triazolecarboxylic acid type (i.e. of the formula B1 in which $W=W3$ and $(X)_n32$ 2,4-$Cl_2$), preferably compounds such as
(B1-6) ethyl 1-(2,4-dichlorophenyl)-5-trichloromethyl-(1H)-1,2,4-triazole-3-carboxylate (frenchlorazole) and related compounds (see EP-A-0174562 and EP-A-0,346,620);

d) Compounds of the dichlorobenzyl-2-isoxazoline-3-carboxylic acid type (i.e. of the formula B1 in which $W=W4$ and $(X)_n=2,4$-$Cl_2$), preferably compounds such as
(B1-7) ethyl 1-(2,4-dichlorophenyl)-2-isoxazoline-3-carboxylate
and related compounds as they are described in WO-91/08202 (International Patent Application No. PCT/EP 90/01966), e) compounds of the dichlorophenylpyrazoline-3-carboxylate type, for example
(B1-8) 3-ethyl 5-t-butyl 1-(2,4-dichlorophenyl)-pyrazolinecarboxylate,
as they are described in WO-91/07874, f) Compounds of the (5-chloro-8-quinolinoxy)acetic acid type (i.e. of the formula B2 in which $(Y)_n=5$-Cl, $Z=OR^1$, $R^*=CH_2$), preferably compounds such as
(B2-1) 1-methylhex-1-yl 2-(5-chloro-8-quinolinoxy)acetate,
(B2-2) 1,3-dimethylbut-1-yl 2-(5-chloro-8-quinolinoxy)acetate,
(B2-3) 4-methylpent-2-yl 2-(5-chloro-8-quinolinoxy)acetate,
(B2-4) 2-heptyl 2-(5-chloro-8-quinolinoxy)acetate,
(B2-5) 1-methylethyl 2-(5-chloro-8-quinolinoxy)acetate,
(B2-6) ethyl 2-(5-chloro-8-quinolinoxy)acetate,
(B2-7) 2-phenoxyethyl 2-(5-chloro-8-quinolinoxy)acetate,
(B2-8) 2-methyl-1-propen-3-yl 2-(5-chloro-8-quinolinoxy)acetate,
(B2-9) 2-methyl-3-oxo-butyl 2-(5-chloro-8-quinolinoxy)acetate,
(B2-10) 2-(pent-3-ylidene-iminooxy)ethyl 2-(5-chloro-8-quinolinoxy)acetate,
(B2-11) 2,2-dimethyl-1,3-dioxolan-4-yl)methyl 2-(5-chloro-8-quinolinoxy)acetate,
(B2-12) (allyoxycarbonyl)methyl 2-(5-chloro-8-quinolinoxy)acetate,
(B2-13) 2-(isopropylideniminooxy)ethyl 2-(5-chloro-8-quinolinoxy)acetate,
(B2-14) trimethylsilylmethyl 2-(5-chloro-8-quinolinoxy)acetate,
(B2-15) 2-(trifluoromethylcarbonylamino)ethyl 2-(5-chloro-8-quinolinoxy)acetate,
(B2-16) 2-(methoxyimino)propyl 2-(5-chloro-8-quinolinoxy)acetate,
(B2-17) 4-(acetoxyimino)pentyl 2-(5-chloro-8-quinolinoxy)acetate,
(B2-18) 2-(benzamido)ethyl 2-(5-chloro-8-quinolinoxy)acetate,
(B2-19) 4-(hydroxyimino)pentyl 2-(5-chloro-8-quinolinoxy)acetate,
(B2-20) 2-(acetoxy)ethyl 2-(5-chloro-8-quinolinoxy)acetate,
(B2-21) 2-(2-methyl-prop-2-en-1-yl)ethyl 2-(5-chloro-8-quinolinoxy)acetate,
(B2-22) 3-(propargyloxy)propyl 2-(5-chloro-8-quinolinoxy)acetate,
(B2-23) N,N-dimethyl-2-(5-chloro-8-quinolinoxy)acetamide,
(B2-24) N-(2-acetoxy-ethyl)-2-(5-chloro-8-quinolinoxy)acetamide,
(B2-25) 2-(allyloxy)propyl 2-(5-chloro-8-quinolinoxy)acetate,
and related compounds as they are described in EP-A-94,349 (US-A4,902,340), EP-A-0191736 (US-A-4,881,966) and German Patent Application P 4041121.4.

The safeners (antidotes of the above groups a) to f) reduce, or inhibit, phytotoxic effects which can occur when the herbicidal compounds A are used in crops of useful plants, without adversely affecting the activity of these herbicides against harmful plants. This allows the field of application of conventional crop protection agents to be considerably widened and extended, for example to crops such as wheat, barley, maize and other Gramineae crops in which the use of the herbicides was hitherto not possible or only possible to a limited extent, i.e. at low dosage rates where the range of activity was narrow.

The herbicidal active substances and the safeners mentioned can be applied together (as a finished formulation or by the tank mix method) or in succession in any desired sequence. The ratio by weight of safener:herbicide can vary within wide limits and is preferably in the range from 1:10 to 10:1, in particular from 1:10 to 5:1. The amounts of herbicides and safeners which are optimal in each case depend on the nature of the herbicide used or on the safener used, and on the species of the plant stand to be treated, and can be determined in each individual case by appropriate preliminary experiments.

The main field of application for using the safeners are especially cereal crops (wheat, rye, barley, oats), rice, maize, sorghum, but also cotton and soya beans, preferably cereals and maize.

Depending on their properties, the safeners of the type B can be used for pretreating the seed of the crop plant (seed dressing) or they can be incorporated into the seed furrows before sowing or applied together with the herbicide before or after emergence of the plants. Pre-emergence treatment includes the treatment of the area under cultivation before sowing and the treatment of the area under cultivation where seed has been sown but where the plants have not emerged yet. Post-emergence application together with the herbicide is preferred. Tank mixes or finished formulations can be employed to this end.

Compared with the seed-dressing method, the method where herbicide and safener are applied together post-emergence represents an important advantage for farming practice. The farmer reduces the costs substantially by applying the substances in a single operation and, above all, labor-intensive seed dressing, which requires a specific seed-dressing apparatus, can be dispensed with. In contrast, the technological requirement for additionally applying the safener is virtually negligible, in particular when herbicide and safener are employed and used in the form of a finished formulation.

The amounts of safener required can vary within wide limits depending on the indication and the herbicide used and are, as a rule, in the range from 0.001 to 5 kg, preferably 0.005 to 0.5 kg, of active substance per hectare.

The present invention therefore also relates to a method of protecting crop plants against phytotoxic secondary effects of herbicidal compounds A, which comprises applying an effective amount of a compound of the above-mentioned formula B1 or B2 prior to, after, or simultaneously with, the herbicide A, preferably together with the herbicide A, post-emergence to the plants, seeds of plants or the area under cultivation.

The compounds B and their combinations with one or more of the abovementioned herbicides can be formulated in many ways, depending on which biological and/or chemico-physical parameters prevail. The following possibilities are therefore suitable for formulation: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water base, oil-miscible solutions, capsule suspensions (CS), dusting agents (DP), seed-dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

The abovementioned formulation types are known in principle and are described, for example in: Winnacker-Küchler, "Chemische Technologie [Chemical Technology]", Volume 7, C. Hauser Verlag Munich, 4th Ed., 1986; Wade van Valkenburg, "Pesticides Formulations", Marcel Dekker N.Y., 2nd Ed. 1973; K. Martens, "Spray Drying Handbook", 3rd ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, such as insecticides, acaricides, herbicides, fungicides, safeners, fertilizers and/or growth regulators may also be prepared on the basis of these formulations, for example in the form of a readymix or as a tank mix.

Wettable powders are preparations which are uniformly dispersible in water and which, besides the active substance and/or safener, also contain surfactants of ionic and/or non-ionic nature (wetting agents, dispersants), for example polyoxethylated alkylphenols, polyoxethylated fatty alcohols, polyoxethylated fatty amines, fatty alcohol polyphenol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate, or alternatively sodium oleoylmethyltaurate, in addition to a diluent or inert substance. To prepare the wettable powders, the herbicidal active substances are ground finely, for example in customary apparatuses such as hammer mills, blowing mills and air-jet mills, and mixed with the formulation auxiliaries either simultaneously of in succession.

Emulsifiable concentrates are prepared by dissolving the active substance and/or safener in an organic solvent, for example butanol, cyclohexanone, dimethylformamide, xylene and also higher-boiling aromatic compounds or hydrocarbons or mixtures of the organic solvents, with the addition of one or more surfactants of ionic or non-ionic nature (emulsifiers). Examples of emulsifiers which can be used are: calcium salts of an alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters such as sorbitan fatty acid esters, polyoxyethylene sorbitan esters such as polyoxyethylene sorbitan fatty acid esters.

Dusting agents can be obtained by grinding the active substance and/or the safener with finely divided solid substances, for example talc, natural clays, such as kaolin, bentonite and prophyllite, or diatomaceous earth.

Suspension concentrates can be oil- or water-based. They can be prepared, for example, by wet grinding by means of commercially available bead mills and, if appropriate, an addition of surfactants as have already been mentioned for example above in the case of the other formulation types.

Emulsions, for example oil-in-water emulsions (EW) can be prepared for example by means of stirrers, colloid mills and/or static mixers using aqueous organic solvents and, if appropriate, surfactants as have already been mentioned for example above in connection with the other formulation types.

Granules can be produced either by spraying the active substance and/or the safener onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

Water-dispersible granules are produced, as a rules, by the conventional processes such as spray-drying, fluidized-bed granulation, plate granulation, mixing by means of high-speed stirrers and extrusion without solid inert material. To produce plate, fluidized-bed, extruder and spray granules, see, for example processes in "Spray-Drying Handbook" 3rd ed. 1979, G. Goodwin Ltd., London; J. E. Browning, "Agglomeration", Chemical and Engineering 1967, pages 147 et seq. "Perry's Chemical Engineer's Handbook", 5th Ed., McGraw-Hill, New York 1973, pp. 8–57.

For more details with regard to the formulation of crop-protection agents see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations contain 0.1 to 99% by weight, in particular 0.1 to 95% by weight, of active substance of the formula (I).

The concentration of active substance in wettable powders is, for example, about 10 to 90% by weight; the remainder to 100% by weight is composed of conventional formulation components. In the case of emulsifiable concentrates, the concentration of active substance can be about 1 to 90, preferably 5 to 80% by weight. Formulations in the form of dusts usually contain 1 to 30, preferably 5 to 20% by weight of active substance, sprayable solutions about 0.05 to 80, preferably 2 to 50% by weight. In the case of water-dispersible granules, the active substance content depends partly on whether the active compound is liquid or solid and on which granulation auxiliaries, fillers etc. are used. Water-dispersible granules contain, for example, between 1 and 95% by weight, preferably between 10 and 80% by weight, of active substance.

In addition, the active substance formulations mentioned contain, if appropriate, the adhesives, wetting agents, dispersing agents, emulsifiers, penetrants, preservatives, antifreeze agents, solvents, fillers, carriers, colorants, defoamers, evaporation inhibitors and pH and viscosity regulators which are conventional in each case.

For use, the formulations, present in commercially available form, are diluted, if appropriate, in the customary manner, for example water in the case of wettable powders, emulsifiable concentrates, dispersions and water-dispersible granules. Preparations in the form of dusts, granules and sprayable solutions are usually not further diluted with other inert substances before use. Particularly good efficacies of the compositions according to the invention can be achieved by adding other wetting agents, in addition to the surfactants contained in the formulations at concentrations from 0.1 to 0.5% by weight by the tank mix method, for example nonionic wetting agents or wetting agents of the fatty alcohol polyol ether sulfate type (see, for example, DE-A-4,029,304=EP-A-0,476,555 or ZA-91/7266).

The application rate of safener required varies, inter alia, with the external conditions such as temperature, moisture and the nature of the herbicide used.

A. Formulation Examples a) A dusting agent is obtained by mixing 10 parts by weight of a compound of the type B or of an active substance mixture of a herbicidal compound A and a safener of the type B and 90 parts by weight of talc as inert substance and comminuting the mixture in a hammer mill.

b) A wettable powder which is readily dispersible in water is obtained by mixing 25 parts by weight of a compound of the type B or of an active substance mixture of a herbicide A and a safener of the type B, 64 parts by weight of kaolin-containing quartz as the inert substance, 10 parts by weight of potassium ligninsulfonate and 1 part by weight of sodium oleoylmethyltaurate as the wetting and dispersing agent, and grinding the mixture in a pinned-disk mill.

c) A dispersion concentrate which is readily dispersible in water is obtained by mixing 20 parts by weight of a compound of the type B or of an active substance mixture of a herbicide A and a safener of the type B with 6 parts by weight of alkylphenol polyglycol ether (®Triton X207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the type B or of an active substance mixture of a herbicide A and a safener of the type B, 75 parts by weight of cyclohexanone as the solvent and 10 parts by weight of oxethylated nonylphenol as the emulsifier.

e) Water-dispersible granules are obtained by mixing

| | |
|---|---|
| 75 parts by weight | of a compound B or an active substance mixture of herbicide A and a safener B. |
| 10 parts by weight | of calcium ligninsulfonate. |
| 5 parts by weight | of sodium lauryl sulfate. |
| 3 parts by weight | of polyvinyl alcohol and |
| 7 parts by weight | of kaolin. | grinding the mixture on a pinned-disk mill and granulating the powder in a fluidized bed by spraying on water as granulation liquid.

f) Alternatively, water-dispersible granules are obtained by homogenizing and precomminuting

| | |
|---|---|
| 25 parts by weight | of a compound B or an active substance mixture of a herbicide A and a safener B, |
| 5 parts by weight | of sodium 2,2'-dinaphthalmethane-6,6'-disulfonate. |
| 2 parts by weight | of sodium oleoylmethyltaurate. |
| 1 part by weight | of polyvinyl alcohol. |
| 17 parts by weight | of calcium carbonate and |
| 50 parts by weight | of water | on a colloid mill, subsequently grinding the mixture on a bead mill and atomizing and drying the resulting suspension in a spray tower by means of a single-substance nozzle.

B. Biological examples

The crop plants, broad-leaf weeds and grass weeds were grown in plastic pots in the field or in the greenhouse until they had reached the four-to five-leaf state and then, post-emergence, treated according to the invention with compounds of Type A) and B). The compounds of type A) and B) were applied in the form of aqueous suspensions or emulsions at an application rate of 300 l of water/ha (converted). 4 weeks after the treatment, the plants were assessed visually for any type of damage by the herbicides applied, and the extent of prolonged damage to the plants was particularly taken into account. The assessment was in percentages in comparison with untreated controls.

The results of Tables 6 and 7 below demonstrate that the compounds of type B, which were used according to the invention, are capable of effectively reducing severe herbicidal damage of crop plants. Even when the herbicides are highly overdosed, severe damage in the crop plants are markedly reduced and lesser damage is compensated for completely. Mixtures of herbicides and compounds of type B are therefore outstandingly suitable for selective weed control in crops such as cereals and maize.

TABLE 6

Greenhouse experiment

| Herbicide [Table/No.] | Safener | Dosage rate [g AS/ha] | % damage on crop plant and weeds | | |
|---|---|---|---|---|---|
| | | | wheat | APSV | GAAP |
| Table 1. | 13 | 1000 | 60 | 93 | 99 |

TABLE 6-continued

Greenhouse experiment

| Herbicide [Table/No.] | Safener | Dosage rate [g AS/ha] | % damage on crop plant and weeds | | |
|---|---|---|---|---|---|
| | | | wheat | APSV | GAAP |
| Ex. No. 20 | | 500 | 55 | 70 | 99 |
| | | 250 | 30 | 60 | 85 |
| | | 125 | 10 | 50 | 75 |
| Table 1. Ex. No. 20 | +B1-1 | 1000 + 1000 | 0 | 95 | 99 |
| | | 500 + 500 | 0 | 90 | 98 |
| | | 250 + 250 | 0 | 80 | 90 |
| | | 125 + 125 | 0 | 70 | 70 |
| Table 1. Ex. No. 20 | +B1-6 | 1000 + 1000 | 0 | 95 | 98 |
| | | 500 + 500 | 0 | 95 | 93 |
| | | 250 + 250 | 0 | 85 | 90 |
| | | 125 + 125 | 0 | 50 | 65 |
| Table 1. Ex. No. 20 | +B2-1 | 1000 + 1000 | 0 | 90 | 97 |
| | | 500 + 500 | 0 | 85 | 94 |
| | | 250 + 250 | 0 | 80 | 90 |
| | | 125 + 125 | 0 | 60 | 75 |
| Table 1 Ex. No. 20 | +B1-7 | 1000 + 1000 | 0 | 90 | 90 |
| | | 500 + 500 | 0 | 80 | 85 |
| | | 250 + 250 | 0 | 75 | 75 |
| | | 125 + 125 | 0 | 70 | 65 |

Ex. of Table 1. No. 20: 2-[2-chloro-4-(methylsulfonyl)benzoyl]-1,3-cyclohexanedione Experimental conditions: Greenhouse experiment; stages of the plants: 4 leaves, or 2 whorls in the case of GAAP.
APSV = *Apera spica venti* = Windgrass
GAAP = *Galium aparine* = Catchweed bedstraw.

TABLE 7

Pot experiment under field conditions

| Herbicide | Safener | Dosage rate [g AS/ha] | Wheat | Barley | Maize |
|---|---|---|---|---|---|
| Table 1. Ex. No. 47 | — | 1000 | 70 | 50 | 70 |
| | | 500 | 50 | 30 | 60 |
| | | 250 | 30 | 20 | 50 |
| | | 125 | 20 | 10 | 30 |
| Table 1. Ex. No. 47 | +B2-2 | 1000 + 1000 | 20 | 20 | 30 |
| | | 500 + 250 | 5 | 10 | 10 |
| | | 250 + 125 | 0 | 0 | 0 |
| | | 125 + 620 | 0 | 0 | 0 |
| Table 1. Ex. No. 47 | +B1-1 | 1000 + 500 | 10 | 20 | 10 |
| | | 500 + 250 | 0 | 0 | 5 |
| | | 250 + 125 | 0 | 0 | 0 |
| | | 125 + 62 | 0 | 0 | 0 |
| Table 1. Ex. No. 48 | | 1000 | 90 | 80 | 95 |
| | | 500 | 80 | 70 | 90 |
| | | 250 | 70 | 60 | 80 |
| | | 125 | 60 | 50 | 70 |
| Table 1. Ex. No. 48 | +B2-1 | 1000 + 500 | 30 | 40 | 30 |
| | | 500 + 250 | 10 | 20 | 5 |
| | | 250 + 125 | 0 | 0 | 0 |
| | | 125 + 62 | 0 | 0 | 0 |
| Table 1. Ex. No. 48 | +B1-2 | 1000 + 500 | 20 | 30 | 40 |
| | | 500 + 250 | 10 | 10 | 10 |
| | | 250 + 125 | 0 | 0 | 0 |
| | | 125 + 62 | 0 | 0 | 0 |

Experimental conditions: 13 cm pot under field conditions; stage of the cereals: beginning of tillering; stage of maize: 4 leaves; assessment: 4 weeks after treatment

We claim:

1. A herbicidal agent which comprises an active amount of
   A) one or more herbicides selected from the group of the 2- acylated, 1,3-dicarbonyl compounds of the formula A or salts thereof

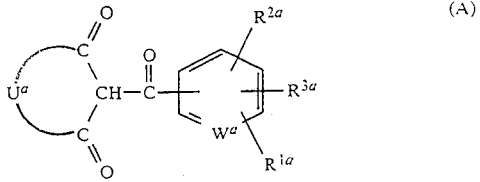

in which
R$^{1a}$ and R$^{3a}$ independently of one another are hydrogen, halogen, (C$_1$-C$_4$-alkyl, (C$_1$-C$_4$-alkoxy, (C$_1$-C$_4$-haloalkyl, (C$_1$-C$_4$-haloalkoxy, CN, NO$_2$, S(O)$_m$R$^{11a}$, NR$^{12a}$R$^{13a}$, NR$^{14a}$C(O)R$^{15a}$, C(O)R$^{16a}$ or OCH$_2$CH$_2$OR$^{21a}$, R$^{2a}$ is halogen, CN, NO$_2$, (C$_1$-C$_4$-alkyl, (C$_1$-C$_4$-alkoxy, (C$_1$-C$_4$-haloalkyl or (C$_1$-C$_4$-haloalkoxy, S(O)$_p$R$^{10a}$, —O—S(O)$_2$R$^{10a}$, N(R$^{20a}$)—S(O)$_2$R$^{19a}$, W$^a$ is CH, R$^{10a}$ is (C$_1$-C$_4$-alkyl, (C$_1$-C$_4$-haloalkyl or (C$_1$-C$_4$-alkoxy, R$^{11a}$ is (C$_1$-C$_4$-alkyl, (C$_1$-C$_4$-haloalkyl, phenyl or benzyl, the last two radicals being unsubstituted or substituted on the phenyl ring, or is NR$^{17a}$R$^{18a}$, R$^{12a}$, R$^{13a}$ independently of one another are hydrogen or (C$_1$-C$_4$-alkyl, R$^{14a}$ is hydrogen or (C$_1$-C$_4$-alkyl, R$^{15a}$ is hydrogen or (C$_1$-C$_4$-alkyl, R$^{16a}$ is hydrogen, (C$_1$-C$_4$-alkyl, (C$_1$-C$_4$-haloalkyl or (C$_1$-C$_4$-alkoxy, R$^{17a}$ and R$^{18a}$ independently of one another are hydrogen or (C$_1$-C$_4$-alkyl, R$^{19a}$ and R$^{20a}$ independently of one another are (C$_1$-C$_4$-alkyl or (C$_1$-C$_4$-haloalkyl, R$^{21a}$ is hydrogen or (C$_1$-C$_4$-alkyl, p is zero or one and U$^a$ is a group of the formula —CR$^{4a}$R$^{5a}$—CR$^{6a}$R$^{7a}$—CR$^{8a}$R$^{9a}$— wherein R$^{4a}$, R$^{5a}$, R$^{6a}$, R$^{7a}$, R$^{8a}$, and R$^{9a}$ are independently selected from hydrogen or C$_1$-C$_4$ alkyl, and B) one or more safener compounds of the formula B1 and B2,

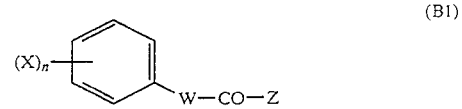

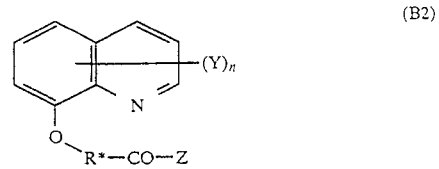

in which
X is hydrogen, halogen, C$_1$-C$_4$-alkyl, C$_1$-C$_4$-alkoxy, nitro or C$_1$-C$_4$-haloalkyl, Y is halogen, C$_1$-C$_4$-alkyl, C$_1$-C$_4$alkoxy, nitro or C$_1$-C$_4$-haloalkyl, R* is —CH$_2$—, Z is OR$^1$, SR$^1$ or NR$^1$R, R independently of R$^1$ is hydrogen, C$_1$-C$_6$-alkyl, C$_1$-C$_6$-alkoxy or phenyl or substituted phenyl or R and R$^1$ together with the nitrogen atom bonded to them are a saturated or unsaturated 3- to 7-membered heterocycle which has at least one nitrogen atom and up to 3 hetero atoms and which is unsubstituted or substituted by radicals selected from the group consisting of $C_1$–$C_4$-alkyl, $C_1$–$C_4$-alkoxy, phenyl or substituted phenyl, $R^1$ independently of R is hydrogen, $C_1$–$C_{18}$-alkyl, $C_3$–$C_{12}$-cycloalkyl, $C_2$–$C_8$-alkenyl or $C_2$–$C_8$-alkynyl, where each of the above carbon-containing radicals independently of one another is unsubstituted or mono- or polysubstituted by radicals selected from the group consisting halogen, hydroxyl, $C_1$–$C_8$-alkoxy, $C_1$–$C_8$-alkylthio, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, cyano, mono- and di-($C_1$–$C_4$-alkyl)-amino, ($C_1$–$C_8$-alkoxy)-carbonyl, ($C_2$–$C_8$-alkenyloxy)-carbonyl, ($C_1$–$C_8$-alkylthio)-carbonyl, ($C_2$–$C_8$-alkynyloxy)-carbonyl, ($C_1$–$C_8$-alkyl)-carbonyl, ($C_2$–$C_8$-alkenyl)-carbonyl, ($C_2$–$C_8$-alkynyl)-carbonyl, 1-(hydroxyimino)-$C_1$–$C_6$-alkyl, 1-($C_1$–$C_4$-alkylimino)-$C_1$–$C_6$-alkyl, 1-($C_1$–$C_4$-alkoxyimino)-$C_1$–$C_6$-alkyl, ($C_1$–$C_8$-alkyl)-carbonylamino, ($C_2$–$C_8$-alkenyl)-carbonylamino, ($C_2$–$C_8$-alkynyl)-carbonylamino, aminocarbonyl, ($C_1$–$C_8$-alkyl)-aminocarbonyl, di-($C_1$–$C_6$-alkyl)-aminocarbonyl, ($C_2$–$C_6$-alkenyl)-aminocarbonyl, ($C_2$–$C_6$-alkynyl)-aminocarbonyl, ($C_1$–$C_8$-alkoxy)-carbonylamino, ($C_1$–$C_8$-alkyl)-aminocarbonylamino, $C_1$–$C_6$-alkalkylcarbonyloxy, which is unsubstituted or substituted by halogen, $NO_2$, $C_1$–$C_4$-alkoxy or optionally substituted phenyl, furthermore consisting of ($C_2$–$C_6$-alkenyl)-carbonyloxy, ($C_2$–$C_6$-alkynyl)-carbonyloxy, $C_1$–$C_8$-alkylsulfonyl, phenyl, phenyl-$C_1$–$C_6$-alkoxy, phenyl-($C_1$–$C_6$-alkoxy)-carbonyl, phenoxy, phenoxy-$C_1$–$C_6$-alkoxy, phenoxy-($C_1$–$C_6$-alkoxy)-carbonyl, phenylcarbonyloxy, phenylcarbonylamino, phenyl-($C_1$–$C_6$-alkyl)-carbonylamino, the 9 last-mentioned radicals being unsubstituted or mono- or poly-substituted in the phenyl ring by radicals selected from halogen, $C_1$–$C_4$-alkyl, $C_1$–$C_4$-alkoxy, $C_1$–$C_4$-haloalkyl, $C_1$–$C$-haloalkoxy and nitro, and furthermore consisting of the formulae $-SiR'_3$, $-OSiR'_3$, $(R')_3Si-C_1-C_6-$alkoxy, $-CO-O-NR'_2$, $-O-N=CR'_2$, $-N=CR'_2$, $-O-NR'_2$, $-CH(OR')_2$ and $-O-(CH_2)_m-CH(OR')_2$, in which the R' in the above mentioned formulae independently of one another are halogen, $C_1$–$C_4$-alkyl or phenyl which is unsubstituted or mono- or polysubstituted by radicals selected from halogen, $C_1$–$C_4$-alkyl, $C_1$–$C_4$-alkoxy, $C_1$–$C_4$-haloalkyl, $C_1$–$C_4$-haloalkoxy and nitro, or the R', as a pair, are a $C_2$–$C_6$-alkylene chain and m is 0 to 6, and furthermore consisting of an alkoxy radical of the formula $R''O-CR'''(OR'')-C_1-C_6$-alkoxy, in which the R'' independently of one another are $C_1$–$C_4$-alkyl or together are a $C_1$–$C_6$-alkylene group and R''' is hydrogen or $C_1$–$C_4$-alkyl, n is an integer from 1 to 5, and W is a divalent heterocyclic radical having 5 ring atoms, of the formula W1 to W4,

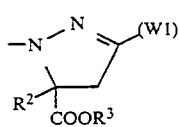
(W1)

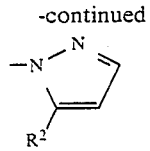
(W2)

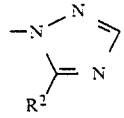
(W3)

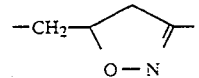
(W4)

in which $R^2$ is hydrogen, $C_1$–$C_8$-alkyl, $C_1$–$C_8$-haloalkyl, $C_3$–$C_{12}$-cycloalkyl or optionally substituted phenyl and $R^3$ is hydrogen, $C_1$–$C_8$-alkyl, $C_1$–$C_8$-haloalkyl, ($C_1$–$C_4$-alkoxy)-$C_1$–$C_4$-alkyl, $C_1$–$C_6$-hydroxyalkyl, $C_3$–$C_{12}$-cycloalkyl or tri-($C_1$–$C_4$-alkyl)-silyl.

2. A composition as claimed in claim 1, wherein $R^1$ is hydrogen, $C_1$–$C_{12}$-alkyl, $C_3$–$C_7$-cycloalkyl, $C_2$–$C_8$-alkenyl or $C_2$–$C_8$-alkynyl, where each of the abovementioned carbon-containing radicals independently of one another is unsubstituted or mono- or polysubstituted by halogen or mono- or disubstituted, by radicals selected from the group consisting of hydroxyl, $C_1$–$C_4$-alkoxy, $C_1$–$C_4$-alkylthio, $C_2$–$C_4$-alkenyloxy, $C_2$–$C_4$-alkynyloxy, mono and di-($C_2$–$C_2$-alkyl)-amino, ($C_1$–$C_4$-alkoxy)-carbonyl, ($C_2$–$C_4$-alkenyloxy)-carbonyl, ($C_2$–$C_4$-alkynyloxy)-carbonyl, ($C_1$–$C_4$-alkyl-carbonyl, ($C_2$–$C_4$-alkenyl)-carbonyl, ($C_2$–$C_4$-alkynyl)-carbonyl, 1-(hydroxyimino)-$C_1$–$C_4$-alkyl, 1-($C_1$–$C_4$-alkylimino-$C_1$–$C_4$-alkyl, 1-($C_1$–$C_4$-alkoxyimino)-$C_1$–$C_4$-alkyl, $C_1$–$C_4$-alkylsulfonyl, phenyl, phenyl-$C_1$–$C_4$-alkoxy, phenyl-($C_1$–$C_4$-alkoxy)-carbonyl, phenoxy, phenoxy-$C_1$–$C_4$-alkoxy, phenoxy-($C_1$–$C_4$-alkoxy)-carbonyl, where the 6 last-mentioned radicals are unsubstituted or mono- or polysubstituted in the phenyl ring by radicals selected from the group consisting of halogen, $C_1$–$C_2$-alkyl, $C_1$–$C_2$-alkoxy, $C_1$–$C_2$-haloalkyl, $C_1$–$C_2$-haloalkoxy and nitro, and radicals of the formulae $-SiR'_3$, $-O-N=CR'_2$, $-N=CR'_2$ and $-O-NR'_2$, in which R' in the abovementioned formulae independently of one another are hydrogen, $C_1$–$C_2$-alkyl or phenyl which is unsubstituted or mono- or polysubstituted by radicals selected from the group consisting of halogen, $C_1$–$C_2$-alkyl, $C_1$–$C_2$-alkoxy, $C_1$–$C_2$-haloalkyl, $C_1$–$C_2$-haloalkoxy and nitro, or, in pairs, are a $C_4$–$C_5$-alkylene chain.

3. A composition as claimed in claim 1, wherein, in the compounds of the formula B1 and B2, X is hydrogen, halogen, methyl, ethyl, methoxy, ethoxy or $C_1$–$C_2$-haloalkyl and Y is halogen, methyl, ethyl, methoxy, ethoxy, or $C_1$–$C_2$-haloalkyl.

4. A composition as claimed in claim 1, wherein, the compounds of the formula B2, Y is halogen or $C_1$–$C_4$-haloalkyl and n is 1, Z is a radical of formula $OR^1$, R* is $CH_2$ and $R^1$ is hydrogen, $C_1$-$C_8$-haloalkyl or ($C_1$-$C_4$-alkoxy)-$C_1$-$C_4$-alkyl.

5. A composition as claimed in any one of claims 2, 3 or 4 wherein, the formula A, $R^{1a}$ and $R^{3a}$ independently of one another are hydrogen, halogen, ($C_1$-$C_4$-alkyl), ($C_1$-$C_4$-alkoxy, ($C_1$-$C_4$-haloalkyl), ($C_1$-$C_3$-haloalkoxy), CN, NO$_2$, $S(O)_m R^{11a}$, $NR^{12a}R^{13a}$, $NR^{14a}C(O)R^{15a}$, $C(O)R^{16a}$, $OCH_2CH_2OR^{21a}$, $R^{2a}$ is halogen, CN, NO$_2$, ($C_1$-$C_4$-alkyl), ($C_1$-$C_4$-alkoxy), ($C_1$-$C_4$-haloalkyl), ($C_1$-$C_4$-haloalkoxy), $S(O)_p R^{10a}$, —O—$S(O)_2 R^{10a}$, $N(R^{20a})$—$S(O)_2 R^{19a}$, $W^a$ is CH, $X^a$ is $CR^{4a}R^{5a}$ or N—$R^{22a}$, $Y^a$ is $CR^{6a}R^{7a}$, carbonyl, oxygen, sulfur, N—$R^{23a}$ or C=CH$_2$, $Z^a$ is $CR^{8a}R^{9a}$, N—$R^{24a}$, oxygen or sulfur, $R^{10a}$ is ($C_1$-$C_4$-alkyl), ($C_1$-$C_4$-haloalkyl) or ($C_1$-$C_4$-alkoxy), $R^{11a}$ is ($C_1$-$C_4$-alkyl), ($C_1$-$C_4$-haloalkyl), phenyl, substituted phenyl, benzyl or $NR^{17a}R^{18a}$, $R^{12a}$ and $R^{13a}$ independently of one another are hydrogen or ($C_1$-$C_4$-alkyl), $R^{14a}$ is ($C_1$-$C_4$-alkyl) or hydrogen, $R^{15a}$ is ($C_1$-$C_4$-alkyl) or hydrogen, $R^{16a}$ is hydrogen, ($C_1$-$C_4$-alkyl), ($C_1$-$C_4$-haloalkyl) or ($C_1$-$C_4$-alkoxy), $R^{17a}$ and $R^{18a}$ independently of one another are hydrogen or ($C_1$-$C_4$-alkyl), $R^{19a}$ and $R^{20a}$ independently of one another are ($C_1$-$C_4$-alkyl) or ($C_1$-$C_4$-haloalkyl), $R^{21a}$, $R^{22a}$, $R^{23a}$ and $R^{24a}$ independently of one another are hydrogen or ($C_1$-$C_4$-alkyl) and m, n and p independently of one another are zero or one.

6. A composition as claimed in claim 5, wherein, in formula A $R^{1a}$ and $R^{3a}$ independently of one another are hydrogen, fluorine, chlorine, bromine, iodine, cyano, nitro, -SO$_3R^{11a}$, $NR^{12a}R^{13a}$, -N(CH$_3$)-C(O)R$^{15a}$, [($C_1$-$C_4$)-alkoxy]-carbonyl, ($C_1$-$C_2$)-alkyl, ($C_1$-$C_2$)-alkoxy, OCH$_2$-CH$_2$-OR$^{21a}$, ($C_1$-$C_2$)-haloalkyl, ($C_1$-$C_2$)-haloalkoxy or ($C_1$-$C_2$)-alkylthio, $R^{2a}$ is fluorine, chlorine, bromine, iodine, cyano, nitro, $S(O)_p R^{10a}$, ($C_1$-$C_3$)-alkyl, ($C_1$-$C_2$)-alkoxy, ($C_1$-$C_3$)-haloalkyl or ($C_1$-$C_2$)-haloalkoxy, $X^a$ is $CR^{4a}R^{5a}$ or N-$R^{22a}$, $Y^a$ is $CR^{6a}R^{7a}$, carbonyl, oxygen, sulfur, N-$R^{23a}$ or C=CH$_2$, $Z^a$ is $CR^{8a}R^{9a}$, N-$R^{24a}$, oxygen or sulfur, $R^{4a}$, $R^{5a}$, $R^{6a}$, $R^{7a}$, $R^{8a}$ and $R^{9a}$ independently of one another are hydrogen, ($C_1$-$C_3$ alkyl), and $R^{21a}$, $R^{22a}$, $R^{23a}$ and $R^{24a}$ independently of one another are ($C_1$-$C_4$)-alkyl.

7. A composition as claimed in claim 6, wherein, in formula A $R^{1a}$ and $R^{3a}$ independently of one another are hydrogen, fluorine, chlorine, bromine, methoxy, ethoxy, methyl, trifluoromethoxy, difluoromethoxy, OCH$_3$CH$_3$OCH$_3$, nitro, trifluoromethyl, methylthio, -SO$_2$CH$_3$, SO$_2$CH$_2$CH$_3$, SO$_2$CH$_2$CH$_2$CH$_3$, SO$_2$CH$_2$Cl, -N(CH$_3$)$_2$, OCH$_2$CH$_2$Cl, OCH$_2$CF$_3$, SO$_2$N(CH$_3$)$_2$, ethyl, n-propyl or [($C_1$-$C_4$)-alkoxy]-carbonyl, $R^{2a}$ is fluorine, chlorine, bromine, iodine, cyano, nitro, $S(O)_p R^{10a}$, ($C_1$-$C_3$)-alkyl, ($C_1$-$C_2$)-alkoxy, ($C_1$-$C_3$)-haloalkyl or ($C_1$-$C_2$)-haloalkoxy, $R^{4a}$, $R^{5a}$, $R^{6a}$ $R^{7a}$, $R^{8a}$ and $R^{9a}$ independently of one another are hydrogen, methyl, and is two.

8. A composition as claimed in claim 1, wherein the ratio by weight of safener B to herbicide A is from 1:10 to 10:1.

9. A composition as claimed in claim 1, which comprises 0.1 to 99 percent by weight of active substances A and B and 1 to 99% by weight of a solid or liquid additive and 0 to 25% by weight of a surfactant.

10. A process for protecting crop plants against phytotoxic secondary effects of herbicides, which comprises applying an effective amount of one or more compounds B (safener) of the type B before, after or simultaneously with the herbicide A to the plants, seeds of the plants or the area under sultivation, wherein the compounds of type B and the herbicides A are as defined in claim 1.

11. The process as claimed in claim 10, wherein the safener B is applied at an application rate of 0.001 to 5 kg/ha of active substance and at a ratio by weight of safener:herbicide of 1:10 to 10:1.

12. The process as claimed in claim 10, wherein the crop plants are cereal plants, maize plants or rice plants.

13. A composition as claimed in claim 1 wherein B) is of the formula B1 and Z is a radical of the formula OR$^1$, NHR$^1$ or N(CH$_3$)R$^1$.

14. A composition as claimed in claim 1 wherein n is an integer from 1 to 3.

15. A composition as claimed in claim 1 wherein the one or more herbicides of the 2-acylated 1,3-dicarbonyl compounds of the formula A) have the formula:

$$\begin{array}{c}\text{[structural formula with substituents } R^{1a}, R^{2a}, R^{3a}, R^{4a}, R^{5a}, R^{6a}, R^{7a}, R^{8a}, R^{9a}, W^a\text{]}\end{array}$$

wherein $R^{1a}$ is SO$_2$CH$_3$ or OCF$_2$H, $R^{2a}$ is Cl or NO$_2$, $R^{3a}$ is H, $R^{4a}$ is H or CH$_3$, $R^{5a}$ is H or CH$_3$, $R^{6a}$ is H, $R^{7a}$ is H, $R^{8a}$ is H, $R^{9a}$ is H and $W^a$ is CH, and, the compound of formula B) is selected from the group consisting of ethyl 1-(2,4-dichlorophenyl)-5-(ethoxycarbonyl)-5-methyl-2-pyrazoline-3-carbonate; ethyl 1-(2,4-dichlorophenyl)-5-methylpyrazole-3-carboxylate; ethyl 1-(2,4-dichlorophenyl)-5-trichloromethyl-(1H)-1,2,4-triazole-3-carboxylate; ethyl 5-(2,4-dichlorobenzyl)-2-isoxazoline-3-carboxylate; 1-methylhex-1-yl 2-(5-chloro-8-quinolinoxy)acetate; and 1,3-dimethylbut-1-yl 2-(5-chloro-8-quinolinoxy)acetate.

* * * * *